(12) United States Patent
Wilder et al.

(10) Patent No.: US 10,463,255 B1
(45) Date of Patent: Nov. 5, 2019

(54) OPTICAL SOURCE FOR DIFFUSE OPTICAL TOMOGRAPHY

(71) Applicant: Cephalogics, LLC, Boston, MA (US)

(72) Inventors: Mark Wilder, Belmont, MA (US); Russell L. Herrig, Lexington, MA (US); Chandran V. Seshagiri, Arlington, MA (US); Bertan Hallacoglu, Boston, MA (US)

(73) Assignee: Invisio Medical, Inc., Winchester, MA (US)

( * ) Notice: Subject to any disclaimer, the term of this patent is extended or adjusted under 35 U.S.C. 154(b) by 20 days.

(21) Appl. No.: 15/478,920

(22) Filed: Apr. 4, 2017

Related U.S. Application Data

(60) Provisional application No. 62/326,225, filed on Apr. 22, 2016.

(51) Int. Cl.
| | | |
|---|---|---|
| *G02B 5/02* | (2006.01) | |
| *A61B 5/00* | (2006.01) | |
| *G02B 19/00* | (2006.01) | |
| *G01J 1/42* | (2006.01) | |
| *G01J 1/04* | (2006.01) | |
| *H01S 5/183* | (2006.01) | |
| *H01S 5/40* | (2006.01) | |

(52) U.S. Cl.
CPC .......... *A61B 5/0073* (2013.01); *G01J 1/0474* (2013.01); *G01J 1/42* (2013.01); *G02B 5/0278* (2013.01); *G02B 19/0014* (2013.01); *G02B 19/0047* (2013.01); *H01S 5/183* (2013.01); *H01S 5/4031* (2013.01)

(58) Field of Classification Search
CPC .............................. H01S 5/183; A61B 5/0073
See application file for complete search history.

(56) References Cited

U.S. PATENT DOCUMENTS

| | | | | |
|---|---|---|---|---|
| 5,936,739 | A | * 8/1999 | Cameron | ........... G01N 21/4795 356/441 |
| 7,643,858 | B2 | * 1/2010 | Agashe | ................ A61B 5/0059 600/310 |
| D763,938 | S | 8/2016 | Muehlemann et al. | |
| D763,939 | S | 8/2016 | Khanicheh et al. | |
| 9,498,134 | B1 | 11/2016 | Trobaugh et al. | |
| 2008/0242958 | A1 | * 10/2008 | Al-Ali | ................ A61B 5/02427 600/323 |
| 2014/0275891 | A1 | 9/2014 | Muehlemann et al. | |
| 2014/0276013 | A1 | 9/2014 | Muehlemann et al. | |
| 2014/0276014 | A1 | 9/2014 | Khanicheh et al. | |

* cited by examiner

*Primary Examiner* — Tony Ko

(74) *Attorney, Agent, or Firm* — Wolf, Greenfield & Sacks, P.C.

(57) ABSTRACT

Optical sources having multiple optical emitters are described, which may be used in a sensor array used to detect optical properties of a subject, including hemoglobin and deoxygenated hemoglobin concentrations. Multiple optical emitters can be positioned within an optical source. The optical source may include a diffuser and one or more optics, which may direct light from the multiple optical emitters along substantially the same optical direction to the diffuser. The diffuser may receive light from the one or more optics and transmit light from the optical source where the transmitted light has a greater angular distribution than light emitted by one of the optical emitters.

13 Claims, 5 Drawing Sheets

OPTICAL SOURCE FOR DIFFUSE OPTICAL TOMOGRAPHY

RELATED APPLICATIONS

The present application claims the benefit under 35 U.S.C. § 119(e) of U.S. Provisional Patent Application Ser. No. 62/326,225 entitled "OPTICAL SOURCE FOR DIFFUSE OPTICAL TOMOGRAPHY," filed Apr. 22, 2016, which is hereby incorporated herein by reference in its entirety.

BACKGROUND

Field

The present application relates to optical sources for optical tomography systems and related apparatus and methods.

Related Art

Diagnostic instruments for monitoring properties of the brain include magnetic resonance imaging (MRI) devices, computed tomography (CT) devices, microdialysis devices, intracranial pressure monitors, cerebral oximeters, transcranial Doppler devices, oxygen catheters, x-ray devices, electroencephalography devices, positron emission tomography devices, single-photon emission computed tomography (SPECT) devices, magnetoencephalography devices, ultrasound devices, and optically-based instrumentation. Some such instruments are placed in proximity to the patient's head. Optically-based sensors for analyzing medical patients are known and optical tomography is a known technique for optically inspecting a specimen.

BRIEF SUMMARY

According to an aspect of the present application an optical source is provided. The optical source comprises a plurality of optical emitters, at least one optic, and a diffuser. The plurality of optical emitters are arranged on a submount and configured to emit light having different characteristic wavelengths in a direction away from the submount. The at least one optic is positioned and configured to direct light from each of the plurality of optical emitters along substantially the same optical direction. The diffuser is positioned on a side of the at least one optic opposite the plurality of optical emitters. The diffuser is configured to receive light from the at least one optic and transmit light from the optical source that has greater angular distribution than the light emitted from the plurality of optical emitters.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
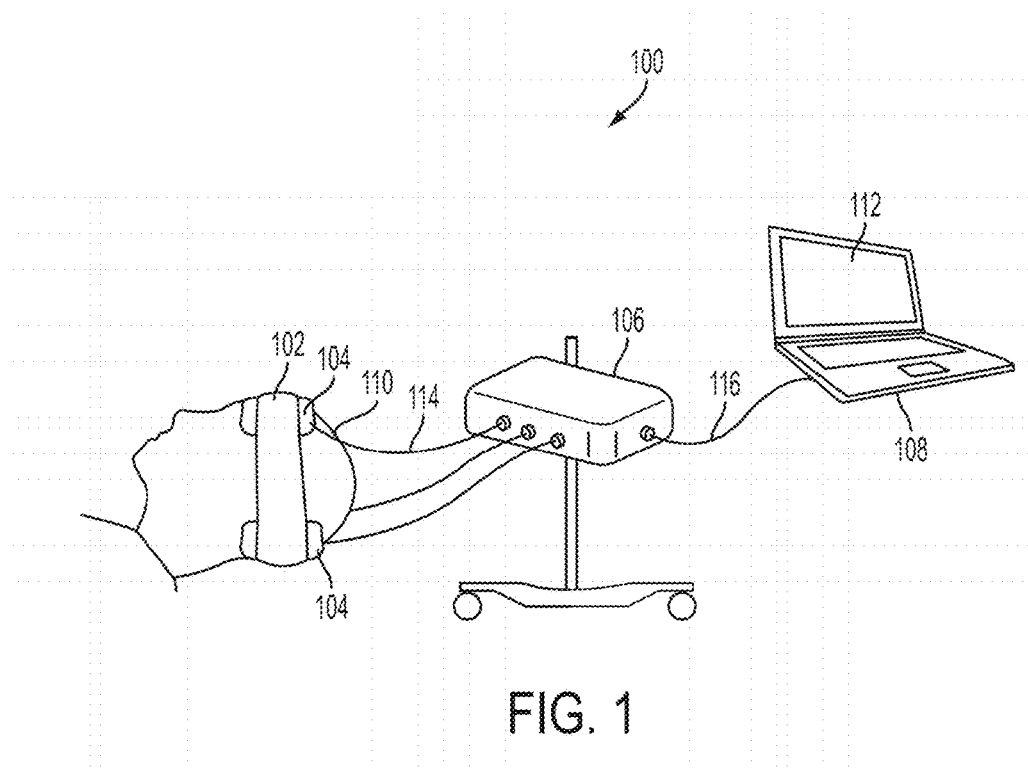
FIG. 1 is a system for performing optical tomography measurements on a subject's head, according to a non-limiting embodiment.

Aspects of the present application relate to an optical source configured to emit light suitable for performing diffuse optical tomography (DOT). A DOT apparatus may include a sensor array of multiple optical sources and multiple optical detectors, which when positioned proximate to a subject (e.g., on the person's head, blood perfused tissue or body part) may perform DOT by emitting light from an optical source of the sensor array and detecting optical signals using the optical detectors of the sensor array. Some existing DOT technology utilizes fiber optic bundle technology where a fiber optic cable propagates light from an optical emitter (e.g., laser) located off of the sensor array to an output end of the cable on the sensor array that acts as an optical source. This type of DOT system configuration allows for optical emitters of the system to be remotely located away from a person's head, which reduces light radiation hazards while providing high optical power to perform DOT. However, fiber optic cables are often bulky and unwieldy to use, which may make use of a DOT apparatus that implements fiber optic bundle technology in a clinical environment impractical.

An optical source of the present application may include one or more optical emitters (e.g., lasers, edge emitting semiconductor lasers, vertical-cavity surface emitting lasers (VCSELs), light emitting diodes (LEDs)), which may improve the practicality of using a DOT apparatus that includes the optical source because the number of cables, and fiber optics cables in particular, that connect to the sensor array are reduced in comparison to a DOT apparatus that utilizes fiber optics bundle technology. The optical source may include one or more substrates where the one or more optical emitters are mounted on the one or more substrates and one or more optics configured to direct light from an optical emitter towards an optical diffuser positioned proximate to the subject being measured. Including the one or more optical emitters in an optical source of a sensor array used for performing DOT may reduce the size and/or weight of the overall DOT apparatus, which may provide benefits particularly in a clinical environment such as improving portability of the sensor array and ease of applying the sensor array to a subject.

The optical source may have an integrated configuration where the one or more optical emitters, the one or more optics, and the optical diffuser are integrated together. In some embodiments, the one or more optical emitters, the one or more optics, and the optical diffuser may be housed within a compact, lightweight, and liquid tight structure (e.g., barrel). In other embodiments, the optical source may have one or more components (e.g., diffuser, optic) configured to detachably couple to other components of the optical source. In some embodiments, the diffuser may be configured to detachably couple to other components of the optical source. The diffuser may be embedded in a liner for the sensor array, such as a disposable liner that is put on the sensor array to perform DOT on each new subject. The liner may be made from a flexible material (e.g., rubber). In such embodiments, the liner may include one or more diffusers positioned at locations corresponding to locations of the one or more optical sources of the sensor array such that when the liner couples to the sensor array a diffuser on the liner aligns with an optical source of the sensor array. An optical source on such a sensor array may include a transparent cover (e.g., glass cover, plastic cover) that interfaces with a diffuser on the liner. In some embodiments, the transparent cover and the diffuser are in contact when the liner is coupled to the sensor array. In some embodiments, the liner may also include a transparent cover for the diffuser. In such embodiments, the transparent cover of the liner may contact the transparent cover of an optical source of the sensor array when the sensor array and the liner are coupled.

Some embodiments of the present application may include a multi-wavelength optical source configured to emit light having a suitably high optical power for performing DOT. The optical source may include multiple optical emitters, where each optical emitter is configured to emit light having a different characteristic wavelength. For each characteristic wavelength, the light emitted by the optical source may have approximately the same light distribution such that light of the characteristic wavelengths overlap. The coincidence of light emitted by the optical source for the different characteristic wavelengths may be achieved by one or more optics included in the optical source. The one or more optics may be positioned relative to the multiple optical emitters such that light transmitted by the one or more optics have overlapping light distributions. In some embodiments, the optical source includes a diffuser positioned to receive light from one or more optical emitters and transmit light having a broader angular distribution than light emitted by an optical emitter alone. In this manner, light emitted by the optical source, regardless of the characteristic wavelength, may be less directional in contrast to light emitted by the optical emitter, such as a laser, alone where the light is highly directional. Such an optical source may meet ocular and skin safety requirements by emitting light with a suitably low optical power. In some embodiments, the irradiance of light emitted by the optical source, measured at a certain distance from the optical source (e.g., 10 cm for ocular safety, 0 cm for skin safety) may satisfy these safety requirements.

Measurements obtained by the optical detectors of the sensor array may be used to determine an optical property of the person, and one or more characteristics of light emitted by an optical source of the present application may improve measurements by the optical detectors and/or analysis of these measurements. One characteristic of light emitted by an optical source is optical power because light optical power emitted by the optical source may impact whether an optical detector positioned at a distance from the optical source detects light from the optical source. Increasing the optical power of the light emitted by the optical source may improve determining one or more optical properties of the person because multiple optical detectors, including optical detectors positioned at different distances from the optical source, may detect light emitted by the optical source, which can improve analysis of measurements obtained by the optical detectors to determine one or more optical properties. Accordingly, an optical source of the present application may include optical emitters configured to provide a suitable optical power such that optical detectors at two or more distances from the optical source can detect light emitted by the optical source.

In some embodiments, an optical source may include one or more directional emitters, such as lasers (e.g., edge-emitting lasers, vertical-cavity surface-emitting lasers (VC-SELs)). One benefit of using a directional emitter in the optical source is it allows for ease in optically manipulating the light beam (e.g., focus) emanating from the directional emitter. In some embodiments, light emitted by the directional emitter may be directed to one or more optics (e.g., lens) of the optical source. In contrast, non-directional emitters (e.g., light emitting diodes (LEDs)) can be challenging to optically manipulate (e.g., focus) the emitted light. Another benefit is that directional emitters may have better electrical power to optical power conversion efficiency than non-directional emitters and, thus, may provide a higher optical output with less heat generation. In the context of lasers, one benefit of using a laser in an optical source is the temporal coherence of the light emitted by the laser where the laser may have a narrower spectral range than a less coherent emitter (e.g., a lamp, a LED), which may improve the ability to determine optical properties from DOT measurements. For example, a laser may have narrower spectral linewidths of approximately 2 nm full width half maximum (FWHM) in comparison to approximately 40 nm for LEDs.

However, aspects of the present application are not limited to implementing directional emitters and techniques described herein may be used with optical sources that include non-directional emitters. In some embodiments, an optical source may include one or more LEDs as optical emitters. In some embodiments, the optical emitter may generally be any optical emitter that provides beams of light with a spectral width less than or equal to approximately 40 nm full width half maximum (FWHM). In some embodiments, the optical emitter may be any optical emitter that provides beams of light with a spectral width in the range of 1 nm FWHM to 50 nm FHWM, or any value or range of values in that range.

Different types and configurations of optical emitters may be employed. In some embodiments, an optical source may include one or more edge-emitting lasers as optical emitters. Edge-emitting lasers may emit light that propagates substantially parallel to the wafer surface of the semiconductor chip and may be reflected and/or coupled out at a cleaved edge. In some embodiments, an optical source may include one or more surface-emitting lasers as optical emitters. Surface-emitting lasers may emit light that propagates in a direction perpendicular to the semiconductor wafer surface. One potential benefit of edge-emitting lasers is that they may be more commercially available and less expensive than surface-emitting lasers, which may reduce costs and improve feasibility of implementing these types of lasers in an optical source.

One aspect of an optical source of the present application includes configuring the optical source to have overlapping light emission areas for light emitted from multiple optical emitters of the optical source. An optical source of the present application may overlap, within the optical source, light beams originating from multiple optical emitters such that the light beams are substantially coincident. Each optical emitter in the optical source may emit a light beam, and the light beams may be overlapped such that the light beams are made substantially coincident. Accordingly, an optical source of the present application may include an optic (e.g., a lens) configured to overlap the light beams emitting from different optical emitters onto another optic (e.g., a diffuser) that transmits the light from the optical source. This overlap can occur at the surface, inside, and/or in the vicinity of the other optic (e.g., diffuser).

Some embodiments of the present application include configuring an optical source that has multiple optical emitters at distinct locations within the optical source to emit light from a common location of the optical source. The techniques of the present application may provide an apparent location (e.g., lateral location) of light emitting from the optical source that is substantially the same for each characteristic wavelength of light emitted by the optical emitters. Accordingly, some embodiments of the present application relate to an optical source having one or more optics positioned to receive light from different optical emitters and redirect the beams from each optical emitter in different directions (e.g., angles) so that they overlap onto a common area or plane. An example may be an array of lenses where each lens of the array acts upon the light coming from a particular optical emitter independently to redirect each light beam to overlap on a common plane. Another example may be a lens array close to the optical emitters to modify the light beam divergence angles before going into a positive lens (e.g., a field lens) that redirects each light beam to overlap on a common area or plane. Alternatively a non-imaging optic system could be used to create the overlap using individual prisms or a faceted optic near the emitters to provide the deviation to overlap the beams. Regardless of the combination of optics used in an optical source, light emitted from the optical source may have substantially the same location of the optical source independent of which optical emitter emitted the light. It should be appreciated that, during operation of the optical source, individual optical emitters may emit light such that the optical source emits light having the characteristic wavelength associated with the respective optical emitter. In embodiments where the multiple optical emitters emit different characteristic wavelengths of light, the optical source may be configured to emit light of each of the different characteristic wavelengths from substantially the same location of the optical source. In this manner, the optical source may emit coincident light for different characteristic wavelengths.

Another aspect of the optical source relates to safety considerations, in particular skin and/or ocular safety, when using the optical source in sensor array to perform DOT measurements on a person. Some optical emitters may emit light having a high radiance ($W \cdot sr^{-1} \cdot cm^{-2}$), and using such optical emitters without managing the irradiance ($W/cm2$) at the skin or ocular surface may cause damage and/or other safety concerns. The optical source of the present application may direct light emitted from the optical source over an area at the optical source output that has a suitably high optical power for performing DOT measurements but is safe for the subject, including safe for exposing the light to the subject's skin. The area of the light emitted by the optical source may depend on one or more optics (e.g., a lens) of the optical source configured to determine the size of the area from the optical source. In some embodiments, the one or more optics of the optical source may direct light beams from multiple optical emitters to overlap within an emissive area at a diffuser of the optical source. The multiple optical emitters may each emit light having a different characteristic wavelength, and the one or more optics may be configured to direct light beams of each characteristic wavelength to overlap within substantially the same emissive area at the diffuser.

An optical source of the present application may include a diffuser configured to broaden the angular distribution of light emitted from the optical source from the angular distribution of light emitted by an optical emitter of the optical source. Light emitted from the optical source may have a suitable angular distribution of light and/or radiance ($W \cdot sr^{-1} \cdot cm^{-2}$) that is safe for eye exposure. In embodiments of optical sources having multiple optical emitters, light beams from the multiple optical emitters incident to the diffuser may overlap on and/or within the diffuser. The diffuser may scatter and re-emit the light in a hemispheric Lambertian, quasi-Lambertian, or diffuse specular optical distribution from the optical source. An optical source of the present application may include multiple optical emitters configured to emit light having different characteristic (e.g., nominal) wavelengths, and the diffuser may be configured to re-emit light of the different characteristic wavelengths in substantially the same light intensity distribution. Such a configuration of the optical source may allow for improved measurements and analysis of measurements to determine optical properties of a person since the location and directionality of light wavelengths emitted by the optical sources relative to the optical detectors can impact the apparent distance between optical sources and optical detectors, which can affect the determination of optical properties of a person, particularly in determining an optical property for different locations within the person. By having light of the different characteristic wavelengths emitted in a similar manner (e.g., location, angular distribution), error associated with variation in emission for different wavelengths in determining optical properties of a person can be reduced.

It should be appreciated that other types of optics or combinations of optics may be included in an optical source to broaden the angular distribution of light. A diffuser is one example of an optic that broadens the angular distribution of light. Other examples include a lens or a combination of lenses configured to broaden the angular distribution of light. Some optical sources may not include a diffuser or other optic to broaden the angular distribution of light emitted by an optical emitter because the angular distribution of light emitted by the optical emitter is sufficient to meet safety concerns. For example, in an optical source that includes an LED an optical emitter, a diffuser may not be necessary because the light emitted by the LED has a suitable radiance to meet safety concerns.

The optical source may emit light having a desired directionality, or reduced directionality in comparison to light emitted by an individual optical emitter of the optical source. Light emitted by an optical emitter and/or incident to a diffuser of the optical source may have an inherent directionality, which is reduced or removed by the light re-emitted by the diffuser. In some embodiments, the optical source is configured to emit light in approximately all directions from an output of the optical source. In such embodiments, light emitted from the optical source may occupy a hemispherical volume, or any other suitable shape or volume, at an output surface of the optical source. In some embodiments, the optical source is configured to emit the light approximately equally in all directions from the optical source.

One or more optics of the optical source may allow for the optical source to act as an effective secondary light source configured to emit light of multiple characteristic wavelengths. Light emitted by the optical source, regardless of the characteristic wavelength of the light, may be coincident across the multiple characteristic wavelengths, and substantially equally diffused upon exiting the optical source. The light emitted from the optical source may have a Lambertian, quasi-Lambertian, or diffuse specular distribution up to a hemisphere (2π steradians) from the optical source. The angular width of the scattered light emitted by the optical source may differ depending on the type of distribution associated with the diffuser used in the optical source. For example, light from an optical emitter has directionality, and an optical source having multiple optical emitters and lacking a diffuser would otherwise emit light in different directions. An optical source having a diffuser configured to emit light having a Lambertian distribution, a quasi-Lambertian distribution, or diffuse distribution may reduce this directionality.

The aspects and embodiments described above, as well as additional aspects and embodiments, are described further below. These aspects and/or embodiments may be used individually, all together, or in any combination of two or more, as the application is not limited in this respect.

A non-limiting example of a system for performing DOT analysis of a subject's head is shown in FIG. 1. System 100 includes a support 102, one or more sensors 104 (two of which are shown), a host module 106 (which may also be referred to herein simply as a "host"), and a central unit 108 (which may be referred to herein as a "master"). The support 102 may support a sensor 104 in relation to the head 110 of a subject (e.g., a medical patient). Thus, the support 102 may represent a headpiece in some embodiments. The system may illuminate the subject's head with optical emissions from the sensor 104 and detect and process optical emissions received from the head, including the original optical emissions emitted by the sensor 104 and/or optical emissions triggered inside the subject in response to original optical emissions from the sensor 104. The host module 106 and central unit 108 may perform various functions, including controlling operation of the sensor 104 and processing the collected data. For example, each of the host module 106 and central unit 108 may include one or more processors, and may perform the various signal processing described further below.

The support 102, sensor 104, host module 106, and central unit 108 of system 100 may take various forms. The sensor 104 may be used non-invasively, and may include suitable components for generating and/or receiving optical signals for performing DOT measurements (using near infrared spectroscopy (NIRS) techniques, for example), including one or more optical sources and/or one or more optical detectors. As shown, the sensor 104 may be configured to optically couple to a subject's head (or other region of interest of a subject), for instance on an external surface of the subject's head (e.g., the scalp) without any need to remove or modify portions of the subject's skull and/or scalp. In some embodiments, the sensor 104 may be flexible to conform to the subject's head. The support 102 may hold or otherwise support the sensor 104 against the subject's head, and may have any suitable construction for doing so.

The host module 106 may be coupled to the sensor 104 by a cabled or wireless connector 114 and may perform various functions with respect to the sensor 104, including controlling operation of the sensor 104 to at least some extent. For example, the host module may communicate control signals to the sensor 104 to control activation of the sensor 104 and/or may receive signals from the sensor 104 representative of the optical signals detected by the sensor 104. The host module 106 may also serve as a communication relay between the sensor 104 and the central unit 108, for example in some embodiments integrating or grouping data (e.g., data packets) from multiple optical detectors into a frame prior to sending to the central unit 108. The host module may be implemented in any suitable form.

The central unit 108, which may be implemented in any suitable form, may be coupled to the host module by a cabled or wireless connection 116 and may perform various control functionality for the system. For example, the central unit 108 may include a user interface via which a user (e.g., a doctor, clinician, or other user) may select the conditions of a test or monitoring event to be performed on the subject. The central unit 108 may provide to the host module 106 suitable control signals relating to the selected test or monitoring event. The host module 106 may, in turn, provide suitable control signals to the sensor 104 to cause production and collection of optical emissions. Collected signals may then be provided to the central unit 108 via the host module 106, and the central unit may, for example, perform post processing of the signals. In some embodiments, the central unit 108 may control display of collected information, for example in textual and/or graphical form on a display 112. In some embodiments, the central unit may control analysis and/or display of images and/or information relating to two or more regions (or portions) of a subject's brain simultaneously (e.g., two hemispheres of the subject's brain).

While the system 100 of FIG. 1 is shown as including a distinct host module 106 and central unit 108, it should be appreciated that not all embodiments are limited in this respect. For example, in some embodiments, the host module 106 and the central unit 108 may be integrated as a single unit.

An optical system for using DOT to analyze a subject, such as system 100 of FIG. 1, may use any suitable sensor 104. An optical array may include a plurality of optical sources and a plurality of optical detectors. The optical sources and optical detectors may be formed on or otherwise connected by a common substrate, which may be flexible in some embodiments, allowing the optical sensor to be placed in contact with, and to conform to, a subject of interest or portion thereof (e.g., a subject's head). Optical sources and optical detectors in the sensor may have any suitable size, shape, and arrangement within the array to perform DOT measurements.

Figure 2A:
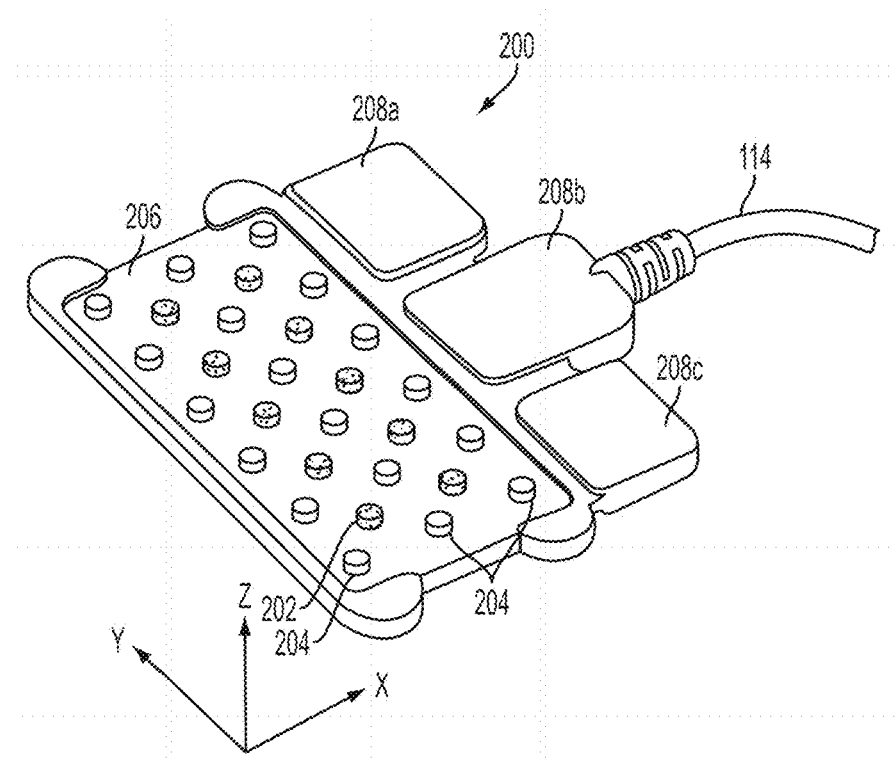
FIGS. 2A and 2B are a top view and a bottom view, respectively, of an optical sensor which may be used in the system of FIG. 1, according to a non-limiting embodiment.
Figure 2B:
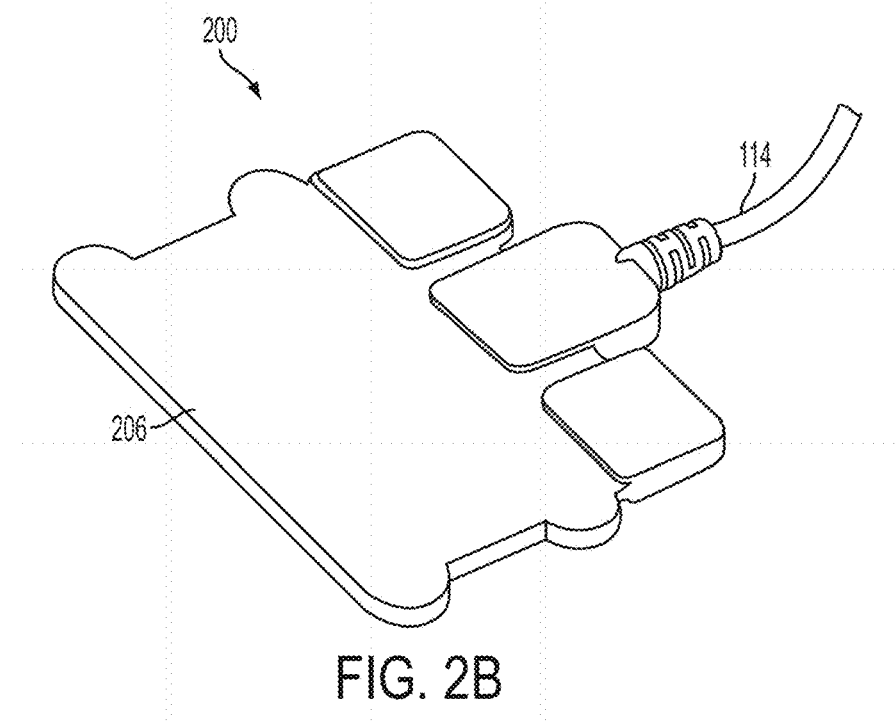

A non-limiting example is illustrated in FIGS. 2A and 2B, which show a top view and bottom view, respectively, of an optical sensor 200 which may be used in the system of FIG. 1, for example as sensor 104, according to a non-limiting embodiment. The sensor 200 includes a plurality of optical sources 202 (shown with dotted fill), totaling ten in all, and a plurality of optical detectors 204, totaling eighteen in all, and which in the non-limiting example illustrated are at least partially encapsulated in a support structure 206. In the non-limiting example of FIG. 2A, the optical sources 202 and optical detectors 204 are arranged in alternating rows that are offset from each other. The optical sensor 200 may further include circuitry 208a, 208b, and 208c, such as analog and/or digital circuitry for controlling operation of and processing of signals from the optical sources 202 and/or optical detectors 204. Optical sensor 200 may be configured to be placed in contact with (or at least in close proximity to) a subject (e.g., a patient), for example on an exterior surface of the subject, such that the optical sources 202 irradiate the subject with optical signals (e.g., near infrared (NIR) signals) and optical detectors 204 receive the optical signals from the subject, which in some embodiments occurs after they pass through the subject.

Figure 3A:
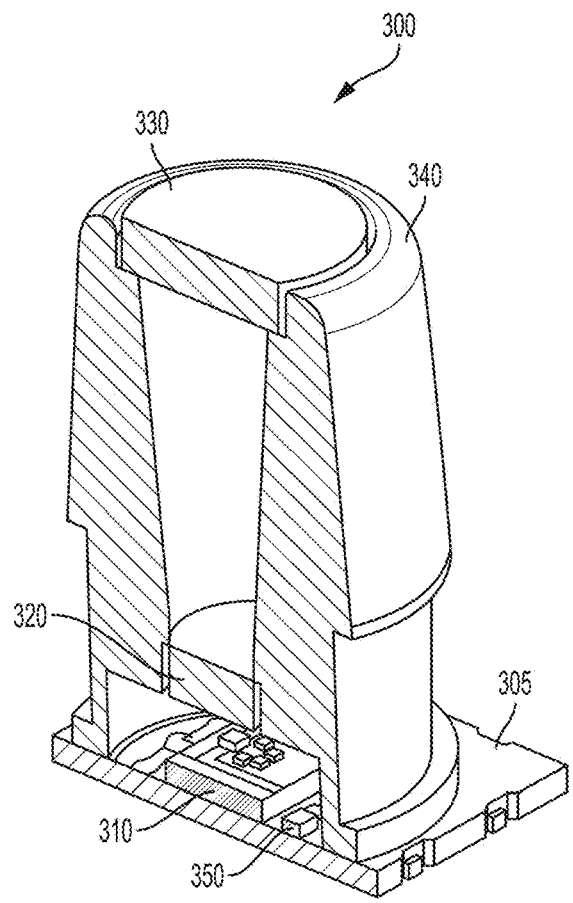
FIG. 3A is a schematic of an optical source which may be used in the optical sensor of FIGS. 2A and 2B, according to a non-limiting embodiment.
Figure 3B:
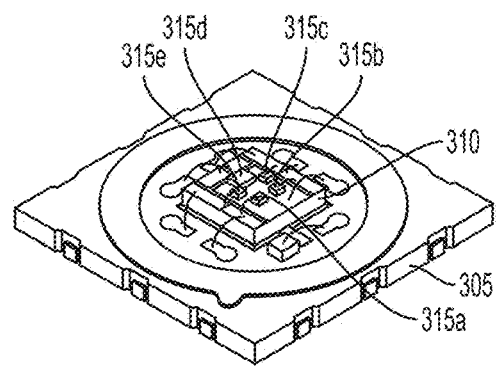
FIG. 3B is a schematic of a substrate having optical emitters mounted on a submount which may be used in the optical source of FIG. 3A, according to a non-limiting embodiment.
Figure 3C:
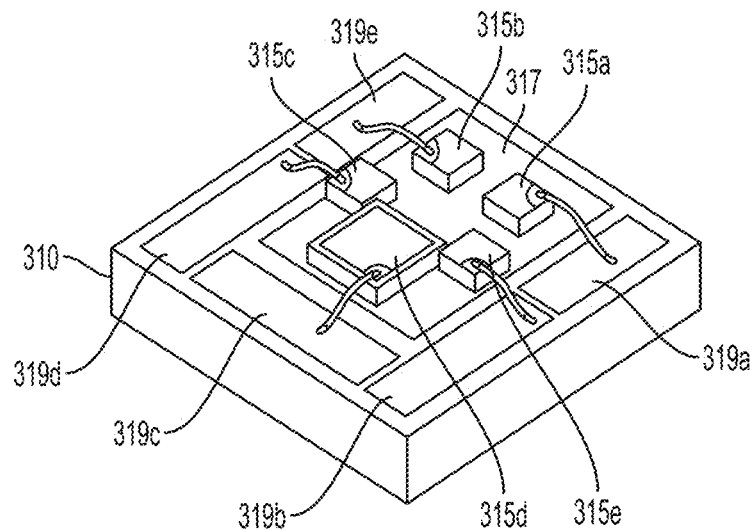
FIG. 3C is a schematic of optical emitters mounted on a submount which may be used in the optical source of FIG. 3A, according to a non-limiting embodiment.
Figure 4:
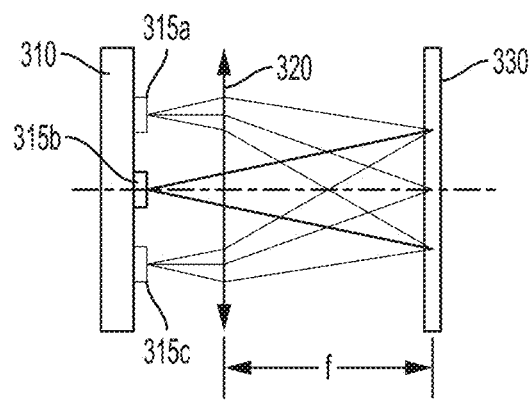
FIG. 4 is a diagram of light propagation through an optical source, such as the optical source of FIG. 3A, according to a non-limiting embodiment.

A non-limiting example of an optical source 300, which may be used in a sensor array for performing DOT analysis, is shown in FIG. 3A. Optical source 300 includes multiple optical emitters 315a, 315b, 315c, 315d, 315e on submount 310, as shown in both FIGS. 3B and 3C. Optical emitters 315a, 315b, 315c, 315d, 315e are configured to emit light having one or more characteristic (e.g., nominal) wavelengths. In some embodiments, each optical emitter is configured to emit light having a different characteristic (e.g., nominal) wavelengths. Submount 310 is mounted onto substrate 305. Optical source 300 may include optic 320 positioned relative to optical emitters 315a, 315b, 315c, 315d, 315e on submount 310 and configured to redirect the light beams from each of the optical emitters 315a, 315b, 315c, 315d, 315e on submount 310 along the same optical direction. Optic 320 is configured to redirect light beams from each of the optical emitters 315a, 315b, 315c, 315d, 315e to substantially overlap at diffuser 330. A schematic of the light path of light emitted by optical emitters 315a, 315b, and 315c being redirected by optic 320 and incident to diffuser 330 is shown in FIG. 4. The relative positioning of optical emitters 315a, 315b, 315c, 315d, 315e, optic 320, and/or diffuser 330 may reduce the impact on the divergence of light beams emitted by the optical emitters.

Characteristics of light emitted by optical source 300 may balance optical power with energy density and/or size of the light emissive area. A larger size of the light emissive area of optical source 300 may provide an optical source configured to measure optical properties of the person over a larger distance since the light beams from the optical emitters diverge over distance. However, the larger the light emissive area of optical source 300, the more potential error in estimating the optical source to optical detector separation distance which may adversely affect the determination of optical properties of the tissue being measured. Additionally, the light emissive area of optical source 300 may reduce skin and/or ocular safety concerns associated with using a sensor array having optical source 300 to perform DOT on a subject. An optical beam emitted by optical source 300 may have a diameter (e.g., the $1/e^2$ Gaussian beam diameter) in the range of 2 to 8 mm or any value or range of values within that range. In some embodiments, the $1/e^2$ Gaussian beam diameter emitted by optical source 300 is in the range of 2.7 mm to 3.0 mm, or any value or range of values within that range.

A light beam from an optical emitter 315 may be substantially centered on diffuser 330. In some embodiments, a light beam from an optical emitter 315 may be offset from a centroid position of diffuser 330 by a distance within a tolerance distance (e.g., 0.05 mm) that still allows light beams from different optical emitters 315a, 315b, 315c, 315d, 315e to substantially overlap at an incident plane of diffuser 330. Optical source 300 may have a configuration that achieves a nominal area of overlapped light beams, which may be considered as a centroid radial offset for the overlapped light beams. In some embodiments, the amount of light beam centroid radial offset between the different optical light beams from the optical emitters incident on diffuser 330 may be in the range of 10 microns to 100 microns, or any value or range of values in that range. In some embodiments, the amount of light beam centroid radial offset may be in the range of in the range of 10 to 50 microns, or any value or range of values in that range.

Optical emitters 315a, 315b, 315c, 315d, 315e may be mounted on (e.g., reside on) submount 310 of optical source 300. Although five optical emitters 315 are shown in FIGS. 3B and 3C, it should be appreciated that optical source 300 may include any suitable number of optical emitters including 2, 3, 4, 5, or 10 optical emitters. In some embodiments, optical emitters 315 include one or more lasers, including vertical-cavity surface-emitting lasers (VCSELs) and/or edge-emitting lasers. An optical emitter 315 may include multiple lasers in an array (e.g., an array of VCSELs). Any suitable number of lasers (e.g., 22, 44) may be in the array that allows for 2 or more arrays to fit without overlapping on submount 310. In some embodiments, one or more optical emitters may include an array of 22 VCSELs and/or an array of 44 VCSELs. In some embodiments, optical emitters 315 may include one or more light-emitting devices (LEDs). Optical emitters 315 may provide the capability to scale optical output of different optical emitters having different spectral characteristics. The optical emitters 315 may have suitable characteristic (e.g., nominal) wavelengths for performing DOT. In some embodiments, optical emitters 315a, 315b, 315c, 315d, 315e may emit light having characteristic wavelengths of 688 nm, 760 nm, 808 nm, 830 nm, and 860 nm. In some embodiments, optical emitters 315a, 315b, 315c, 315d, 315e may emit light having characteristic wavelengths of 688 nm, 760 nm, 808 nm, and 850 nm. It should be appreciated that this is a non-limiting example of characteristic wavelengths and that optical emitters 315 may emit other suitable characteristic wavelengths. An angular emission divergence of an optical emitter may be in the range of 10 degrees to 30 degrees full width at $1/e^2$ Gaussian intensity, or any value or range of values in that range. In some embodiments, an optical emitter 315 may have an angular emission divergence of approximately 19 degrees full width at $1/e^2$ Gaussian intensity. It should be appreciated that an optical emitter having any suitable angular emission divergence may be used in optical source 300. The aperture of an optical emitter 315 may have a diameter in the range of 5 microns to 1 mm, or any value or range of values in that range. In some embodiments, the aperture of an optical emitter 315 may have a diameter of approximately 12 microns. In embodiments where an optical emitter is an LED, the diameter of an aperture may be approximately 1 mm.

Submount 310 may have any suitable configuration for arranging and positioning optical emitters 315 within optical source 300. The optical emitters 315a, 315b, 315c, 315d, 315e may be positioned in any suitable arrangement within the area of submount 310. Optical emitters 315 may be positioned within the area defined by the perimeter of submount 310. Submount 310 may electrically couple with optical emitters 315 and provide control signals to one or more optical emitters 315. Submount 310 may include one or more anodes and one or more cathodes electrically coupled to optical emitters 315. As shown in FIG. 3C, anodes 319a, 319b, 319c, 319d, 319e are electrically coupled to optical emitters 315a, 315b, 315c, 315d, 315e, respectively. Each of the optical emitters 315a, 315b, 315c, 315d, 315e are electrically coupled to cathode 317. In some embodiments, submount 310 may have a planar configuration. In other embodiments, submount 310 may have non-planar configuration. Optical emitters 315 may be positioned on submount 310 within a bolt circle, which may have a radius in the range of 0.25 mm to 2 mm, or any value or range of values in that range.

Submount 310 may be mounted on substrate 305, such as by using a suitable epoxy (e.g., Epotek 353ND). Electrical connections between submount 310 and substrate 305 such that optical emitters 315 are electrically coupled to substrate 305 via submount 310. For example, anodes 319a, 319b, 319c, 319d, 319e and/or cathode 317 shown in FIG. 3C may electrically couple with substrate 305. Submount 310 and/or substrate 305 may have suitable thermal properties configured to maintain a level of thermal stability of the wavelength emission by optical emitters 315a, 315b, 315c, 315d, 315e. Submount 310 and/or substrate 305 may be configured to provide substantially similar thermal stability to each of the optical emitters 315. Submount 310 and/or substrate 305 may prove thermal stability in the range of 0.5° C. to 4° C. variation across submount 310. Substrate 305 may comprise a printed circuit board (PCB), and the type of PCB may impact the thermal properties of the optical source 300, including the thermal stability of wavelength emission by optical emitters 315a, 315b, 315c, 315d, 315e. In some embodiments, submount 310 may include an alumina base having copper traces.

Optic 320 of optical source 300 may be positioned relative to the optical emitters 315a, 315b, 315c, 315d, 315e on submount 310 to receive light emitted from the optical emitters. Optic 320 may direct and/or redirect light to be substantially coincident such that light from the different optical emitters 315a, 315b, 315c, 315d, 315e on submount 310 substantially overlap on an incident surface of diffuser 330. In embodiments where optic 320 is a single positive lens, positioning of optic 320 closer to an optical emitter 315 may reduce the impact of individual optical emitter beam divergence on the optical source. Optic 320 may be positioned at a distance from optical emitters 315a, 315b, 315c, 315d, 315e in the range of 100 microns to 700 microns, or any value or range of values in that range. In some embodiments, optic 320 is positioned at a distance from optical emitters 315a, 315b, 315c, 315d, 315e of approximately 200 microns. Optic 320 may be a suitable lens with an effective focal length in the range of 5 mm to 15 mm, or any value or range of values in that range. An example of a suitable lens is Edmund Optics 45-963, which has an effective focal length of 9.0 mm. Centering of the lens within barrel 340 may be less than approximately 75 microns, or within a range of 0 to 100 microns, or any value or range of values in that range.

It should be appreciated that although one optic 320 configured to redirect light from multiple optical emitters to a diffuser is shown in FIGS. 3A and 4 any suitable number and/or configuration of optics may be used in an optical source of the present application. In some embodiments, optic 320 may be a lens array such that the light from each optical emitter is treated individually to effect optimal light beam overlap at the diffuser 330. In some embodiments, optic 320 may be a lens array in combination with a positive lens (e.g., a field lens). In such embodiments, the lens array may be positioned before the positive lens. In some embodiments, optic 320 is a negative lens in combination with (e.g., positioned before) a positive lens, which may increase the divergence of light beams prior to overlapping of the light beams. It should be appreciated that other combinations of optics may be utilized as well for optic 320 and that these are non-limiting examples.

Optical source 300 may include diffuser 330 positioned on a side of optic 320 opposite from optical emitters 315a, 315b, 315c, 315d, 315e and configured to receive light from optic 320. Diffuser 330 of optical source 300 may provide a suitable distribution of light by broadening the angular distribution of the light directed by optic 320. Diffuser 330 may be transmissive to light emitted by one or more optical emitters 315. Diffuser 330 may be positioned relative to optic 320 such that diffuser 330 is separated from optic 320 by approximately one back focal distance of optic 320, as shown in FIG. 4. The distance of optical emitters 315a, 315b, 315c, 315d, 315e to diffuser 330 may be in the range of 5 mm to 15 mm, or any value or range of values in that range. In some embodiments, the distance between optical emitters 315 and diffuser 330 is approximately 9.5 mm. Light incident on diffuser 330 may have a spot diameter in a range of 2 mm to 8 mm, or any value or range of values in that range. The spot diameter of light incident on diffuser 330 may impact the distribution of light re-emitted by diffuser 330. In some embodiments, diffuser 330 may provide a $1/e^2$ (87%) Gaussian distribution for a spot diameter of approximately 2.9 mm of light emitted by an optical emitter 315. Diffuser 330 may include one or more materials, and the type of material of diffuser 330 may impact the light intensity exiting diffuser 330, which may improve overall efficiency of the optical source 300. Materials that may be included in diffuser 330 include opal glass, glass with embedded microbubbles, ground glass, or any suitable material providing transmissive optical diffusion characteristics. Diffuser 330 may have a transmission in the range of 30% and 70%, or any value or range of value within that range. In some embodiments, diffuser 330 may have approximately 50% transmission. Diffuser 330 may have a diameter of in the range of 2 mm to 8 mm, or any value or range of values in that range. In some embodiments, diffuser 330 has a diameter of approximately 4 mm. Diffuser 330 may have a thickness of in the range of 0.5 mm to 2 mm, or any value or range of values in that range. In some embodiments, diffuser 330 may have a thickness of approximately 1 mm.

Barrel 340 of optical source 300 is mounted to substrate 305. Barrel 340 may have an inner surface with a tapering inner diameter. The taper may be either inward or outward. Barrel 340 may taper outwardly from optic 320 to diffuser 330. Alternatively barrel 340 may be straight or taper inwardly. Air may fill the region between optic 320 and diffuser 330. The inner surface of barrel 340 may have a smaller diameter at optic 320 than at diffuser 330, or a larger diameter at optic 320 than at diffuser 330, or be of the same diameter at optic 310 and diffuser 330. Barrel 340 may be attached to substrate 305 using a hermetic or a non-hermetic seal and may be electrically grounded through its attachment. At the exposed surface of the optical source, the diffuser 330 may be flat in some embodiments. The diffuser 330 may be convex in other embodiments. In some embodiments, diffuser 330 is positioned flush with an opening of barrel 340. In other embodiments, diffuser 330 is positioned to extend beyond a side of barrel 340 by a distance (e.g., less than 0.3 mm). Barrel 340 may have a length, L1, (along the direction of light through barrel 340) in the range of 3 mm to 15 mm, or any value or range of values in that range. The optical path from optical emitters 315a, 315b, 315c, 315d, 315e on submount 310 to diffuser 330 may be in the range of 5 mm to 15 mm, or any value or range of values in that range. In some embodiments, the optical path from optical emitters 315 to diffuser 330 may be in the range of 9 mm to 10 mm, or any value or range of values in that range.

Figure 5:
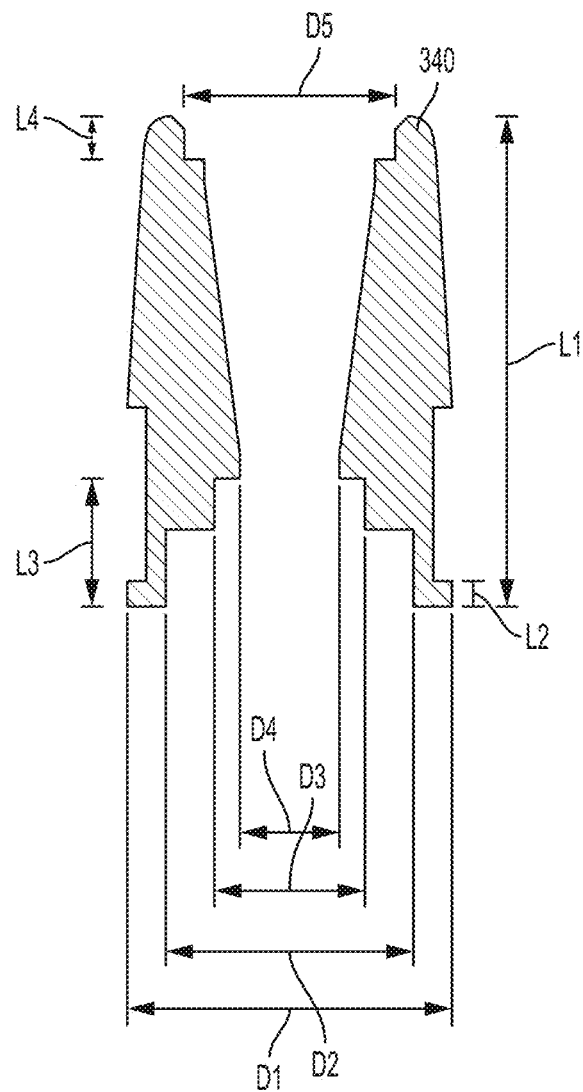
FIG. 5 is a cross-sectional view of a barrel which may be used in the optical source of FIG. 3A, according to a non-limiting embodiment.

FIG. 5 is a cross-sectional schematic of barrel 340 with several dimensions of barrel 340. In some embodiments, barrel 340 may have a length L1 in the range 6 mm to 15 mm, or any value or range of values in that range. In some embodiments, barrel 340 may have length L1 in the range 9 mm to 11 mm, or any value or range of values in that range. Barrel 340 may have external features that include a flange. The flange may have an outer diameter D1 within the range of 5 mm to 8 mm, or any value or range of values in that range, and a height L2 within the range of 0.2 mm to 1 mm, or any value or range of values in that range. The inner diameter D2 of barrel 340 may be within a range of 3 mm to 8 mm, or any value or range of values in that range. In some embodiments, the inner diameter D2 of barrel 340 may be approximately 4.75 mm. Barrel 340 may have inner diameter D3 to accommodate optic 320, which may be in a range of 2 mm to 5 mm, or any value or range of values in that range. Optic 320 may be positioned within barrel 340 such that a surface of optic 320 is a distance L3 from the side of the barrel 340 proximate the optical emitters 315. Distance L3 of barrel 340 may be in the range 1 mm to 4 mm, or any value or range of values in that range. Barrel 340 may have a tapered inner surface having an inner diameter D4 at the narrowest section of the tapered inner surface. Inner diameter D4 of barrel 340 may be in the range 1 mm to 3 mm, or any value or range of values in that range. Barrel 340 may have region to accommodate diffuser 330 having an inner diameter D5 and length L4. Inner diameter D5 may be in the range 3 mm to 6 mm, or any value or range of values in that range. Length L4 may be in the range of 0.4 mm to 2 mm, or any value or range of values in that range. In some embodiments, barrel 340 may have diameter D1 be approximately 6.5 mm, diameter D2 be approximately 5 mm, diameter D3 be approximately 3.05 mm, diameter D4 be approximately 2.05 mm, diameter D5 be approximately 4.175 mm, length L1 be approximately 9.85 mm, length L2 be approximately 0.15 mm, length L3 be approximately 2.54 mm, and length L4 be approximately 0.85 mm.

Optic 320 and diffuser 330 may be mounted to barrel 340 using a suitable epoxy (e.g., Epotek 353ND, Epotek 353ND-Black). Barrel 340 may be mounted on substrate 305 and may house submount 310 and optic 320. In some embodiments, barrel 340 may be metal enclosure sized and shaped to accommodate the components of optical source 300. In some embodiments, barrel 340 may have a cylindrical shape either having a custom manufactured size or a standardized size (e.g., standardized semiconductor package, such as a TO-type can). Barrel 340 may be mounted on substrate 305 using a suitable epoxy (e.g., Epotek 353ND). Conductive epoxy (e.g., Epotek H20E) may be used to form electrical connections, which may act as a ground connection. Alternatively, the barrel 340 may be attached to substrate 305 by brazing or by using a laser weld to obtain a conductive connection.

A temperature sensor 350 positioned proximate to optical emitters 305 may be mounted on substrate 305. Optical source 300 may have a capacity to handle (e.g., dissipate) a heat load of in the range of 5 and 25 mW, or any value or range of values in that range such that the temperature of optical source 300 does not exceed 41° C. during operation under normal conditions. In some embodiments, optical source 300 may have a capacity to handle a heat load of approximately 15 mW. Temperature sensor 350 may measure the temperature proximate to the optical emitters 315*a*, 315*b*, 315*c*, 315*d*, 315*e*. The measured temperature may provide an indication of change to the characteristic wavelengths emitted by optical emitters 315*a*, 315*b*, 315*c*, 315*d*, 315*e* because the wavelengths of light emitted by optical emitters 315*a*, 315*b*, 315*c*, 315*d*, 315*e* may shift with changes in temperature, and the indication of the change may provide an indication of how to shift calibration measurements of the characteristic wavelengths. The optical power of optical source 300 may decrease with increasing temperature so temperature may be used to re-estimate optical power from a previously obtained calibration measurement of optical power. In some embodiments, temperature sensor 350 is a thermistor. The thermistor may have a resistance of approximately 10 kΩ and may have a sensitivity of between 1-2%. Any suitable thermistor or other temperature measuring component may be used as tempera-ture sensor 350. The temperature sensor may be epoxy bonded to substrate 305 using a suitable epoxy (e.g., Epotek H20E).

Substrate 305 may have suitable thermal properties to remove heat from optical emitters 315*a*, 315*b*, 315*c*, 315*d*, 315*e* on submount 310 by acting as a heat sink, which may impact the stability of the spectral range of light emitted by optical emitters 315. Substrate 305 may prove thermal stability in the range of 0.5° C. to 4° C. variation across substrate 305. In some embodiments, the substrate material may provide less than approximately 2° C. variation across substrate 305. In some embodiments, substrate 305 is a ceramic substrate. In other embodiments, substrate 305 is PCB material, such as FR-4 glass epoxy. The high thermal conductivity of submount 310 may be continued on through the submount 305 by contact with copper planes on either or both 310 and 305.

Some embodiments of the present application relate to methods of operating a sensor array having optical sources according to the technology described herein. The sensor array, such as sensor array 200, may have multiple optical sources, such as optical source 300, arranged on the sensor array along with multiple optical detectors configured to detect light emitted by the multiple optical sources. Operation of the sensor array may include providing control signals to each of the optical sources of the sensor array to control light emission by the optical sources. The control signals may control an individual optical emitter of the sensor array to emit light or turn "on." The optical detectors of the sensor array may detect any light associated with the optical emitter. In embodiments where an optical emitter is configured to emit multiple characteristic wavelengths of light, operating the sensor array may include controlling each optical emitter to sequentially emit light having one of the multiple characteristic wavelengths before controlling each optical emitter to sequentially emit light having a different characteristic wavelength. Such a method of operating the sensor array may reduce or prevent heat build-up within each optical source and within the sensor array by allowing time between each use of an optical source as other optical sources are controlled to emit light. The optical emitters may be driven (e.g., powered) to obtain approximately the same optical power for each nominal wavelength, or may be individually driven to obtain different optical powers depending on wavelength. Certain optical power versus wavelength configurations may be used to take into account different scattering and absorption properties of the subject and thus be tailored in a manner to be advantageous in determining optical properties of a subject.

An example method of operation of a sensor array having 10 optical sources where each optical source has 5 optical emitters is described in further detail. First, a "dark" measurement may be obtained from the optical detectors with all optical sources turned "off" and emitting no light. Second, the optical sources are controlled to sequence through each of the five optical emitters across all the optical sources. In this example, the method may sequence through each of optical sources 1 through 10 with only optical emitter 1 turned "on." Next, the method may sequence through each of optical sources 1 through 10 with only optical emitter 2 turned "on." Next, the method may sequence through each of optical sources 1 through 10 with only optical emitter 3 turned "on." Next, the method may sequence through each of optical sources 1 through 10 with only optical emitter 4 turned "on." Then, the method may sequence through each of optical sources 1 through 10 with only optical emitter 5 turned "on." This process may be repeated for any suitable number as part of performing DOT measurements. It should be appreciated that this optical source and optical emitter time sequencing may be generalized for different numbers of optical sources and different numbers of optical emitters within each optical source. In this example, only one optical source in a sensor array may be "on" at a time, and within an optical source only one optical emitter may be "on" at a time. Other suitable methods of optical source and optical emitter operation may be used to operate a sensor array for performing DOT measurements.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

What is claimed is:

1. An optical source comprising:
   a plurality of optical emitters arranged on a substrate and configured to emit light having different characteristic wavelengths in a direction away from the substrate;
   at least one optic positioned and configured to direct light from each of the plurality of optical emitters along substantially the same optical direction; and
   a diffuser positioned on a side of the at least one optic opposite the plurality of optical emitters, wherein the diffuser is configured to receive light from the at least one optic and transmit light from the optical source that has greater angular distribution than the light emitted from the plurality of optical emitters, and wherein the diffuser transmits the light in a forward direction,
   wherein the at least one optic includes a positive lens having a focal length, and the diffuser is positioned within the optical source at a distance from the positive lens equal to approximately the focal length.

2. The optical source of claim 1, wherein the plurality of optical emitters includes a plurality of lasers.

3. The optical source of claim 2, wherein the plurality of lasers includes a plurality of vertical-cavity surface-emitting lasers (VCSELs).

4. The optical source of claim 2, wherein the plurality of lasers includes a plurality of edge emitting lasers.

5. The optical source of claim 1, wherein the diffuser is a transmissive diffuser.

6. The optical source of claim 1, wherein the diffuser is configured to transmit the light from the optical source in a Lambertian distribution.

7. The optical source of claim 1, wherein the diffuser is configured to transmit the light from the optical source in a quasi-Lambertian distribution.

8. The optical source of claim 1, wherein the at least one optic further includes a negative lens positioned between the positive lens and the plurality of optical emitters.

9. The optical source of claim 1, wherein the at least one optic further includes a lens array positioned between the positive lens and the plurality of optical emitters.

10. The optical source of claim 1, wherein the at least one optic is configured to direct light emitted by each of the plurality of optical emitters to overlap in a common plane at the diffuser.

11. The optical source of claim 1, wherein the at least one optic is configured to direct light emitted by each of the plurality of optical emitters to be substantially coincident at the diffuser.

12. The optical source of claim 1, wherein the at least one optic is configured to direct light emitted by each of the plurality of optical emitters to overlap in a common plane beyond the diffuser.

13. A sensor array comprising a plurality of optical sources and a plurality of optical detectors, wherein the plurality of optical sources comprises the optical source of claim 1.

\* \* \* \* \*